United States Patent
Bendis

[11] Patent Number: 6,080,100
[45] Date of Patent: Jun. 27, 2000

[54] PROPHYLACTIC SYSTEM WITH VASODILATOR-CONTAINING FILM

[76] Inventor: Ina K. Bendis, 1436 Aura Way, Los Altos, Calif. 94024

[21] Appl. No.: 08/771,229

[22] Filed: Dec. 20, 1996

Related U.S. Application Data

[60] Provisional application No. 60/008,924, Dec. 20, 1996.

[51] Int. Cl.[7] .................................................. A61F 5/00
[52] U.S. Cl. ............................................. 600/38; 128/844
[58] Field of Search ................. 128/842–44; 600/38–41

[56] References Cited

U.S. PATENT DOCUMENTS

| | | | |
|---|---|---|---|
| 4,332,243 | 6/1982 | Gutnick | 128/844 |
| 4,829,991 | 5/1989 | Boeck | 128/844 |
| 5,333,621 | 8/1994 | Denzer | 128/842 |
| 5,421,350 | 6/1995 | Friedman | 128/842 |
| 5,458,114 | 10/1995 | Herr | 128/842 |
| 5,626,149 | 5/1997 | Schwartz | 128/842 |

*Primary Examiner*—John P. Lacyk
*Attorney, Agent, or Firm*—Kolisch Hartwell Dickinson McCormack & Heuser

[57] ABSTRACT

A prophylactic system includes a vasodilator-containing film for use on a patient's, or user's, body. The prophylactic system includes a first expanse of expandable support material constructed for attachment to a desired section of such a patient's body. A vasodilator-containing film is formed over substantially the entire inner surface of the support material. The first expanse of may be formed as one of the group consisting of a patch, strip, tape, sheath, or condom. In a first preferred embodiment, the first expanse is formed as a sheath and is constructed for enclosing a protuberant section of the patient's body such as an appendage, penis, finger, toe, or ear. Other versions include a second expanse of expandable support material, with the first expanse being formed as a patch, strip, or tape, and the second expanse being formed as a sheath or condom. There is also a condom-like system includes a sheath, and vasodilator-containing material. The sheath is formed as a composite, and includes an inner layer formed of the vasodilator-containing material, a first reservoir that holds a preselected amount of the vasodilator-containing material, and a breakable internal membrane defining an inner boundary of the reservoir. The sheath also preferably includes a second reservoir for holding penile ejaculate, with the first and second reservoirs formed as one reservoir with two compartments. A combination method of promoting vasodilation of a penis to facilitate penile erection, and preventing conception includes the steps of applying a vasodilator-containing material topically to such penis to produce a penile erection, and fitting a prophylactic over such penis after such penile erection is produced.

14 Claims, 1 Drawing Sheet

PROPHYLACTIC SYSTEM WITH VASODILATOR-CONTAINING FILM

This application claims the benefit of U.S. Provisional Application No. 60/008,924, filed Dec. 20, 1996.

BACKGROUND AND SUMMARY OF THE INVENTION

The present invention relates generally to medical products in the form of chemical agents that increase blood flow. More particularly, the invention concerns a novel prophylactic system with a vasodilator-containing film, which system is useful to treat impotency and other diseases or physical conditions where treatment requirements include increased blood flow.

It is known that impotency occurs in a substantial portion of the male population. Impotency takes two forms, physiological and psychological. A male who has psychological impotency is physically capable of having an erection, but unable to achieve the same for psychological reasons.

There have been a number of conventional proposals for diagnosing the particular form of impotency and treating the psychological form. In connection with such treatments, U.S. Pat. No. 4,829,991 to Boeck describes a condom with an interior surface coated with a transdermal nitroglycerin (NTG) coating, a known vasoactive dilator. The idea is for a male to stimulate an erection in his penis by placing the NTG-coated condom over it.

There are several drawbacks to the condom proposed by Boeck. First, that condom will not stimulate an erection in a number of males with psychological impotency because the construction of the condom requires that the male user's penis be sufficiently erect to use it. In other words, the Boeck proposal surprisingly requires that the condom user has the very capability the user lacks, and for which the user is seeking treatment. A substantial percentage of males with psychological impotency cannot achieve the requisite degree of penile erection to use the Boeck condom.

A further, essential drawback with Boeck is that it proposes coating the interior surface of the condom with conventional transdermal NTG adhesive coating or patch. There is no clinical evidence that such convention transdermal NTG adhesive coatings are effective to release transdermally an effective amount of NTG into the user's blood.

Other conventional proposals involve topically applying NTG-containing cream directly to the penis before intercourse. The essential drawback with such proposals is that the NTG present on the user's penis is transmitted to the user's sexual partner, and that NTG can have deleterious health effects on the user's sexual partner.

With respect to other diseases or physical conditions where treatment requirements include increased blood flow, conventional proposals have been lacking in showing devices or methods to increase blood flow noninvasively and effectively. One example of such diseases and conditions is known as Raynaud's syndrome which involves vasoconstriction of blood vessels in the fingers and toes. The result is to cause affected appendages to become cold, dry, painful, and unattractive in appearance. Another example of such diseases and conditions is frostbite.

Until now, there has been no effective proposal to promote blood flow to treat psychological impotency and such other diseases and conditions.

Accordingly, it is a principal object of the present invention to provide a device and treatment method that overcomes the drawbacks of prior-art proposals.

Yet another object is to provide such device and method that is usable by male users who lack the ability of achieving enough of a penile erection to use a condom.

Another object is to provide such device and method that is usable to treat Raynaud's syndrome.

Yet another object is to provide such device and method that is usable to treat frostbite.

Another important object of the invention is to provide such device and method that promotes penile erection in males but also provides other health advantages.

Still another object is to provide such device and method that encourages the use of condoms among males who have psychological impotency as a way of diminishing the occurrence of unwanted pregnancies and/or sexually transmitted diseases in the males' sexual partners.

Another object is to provide such device and method that tends to prevent heart attacks during sexual intercourse in males who have both psychological impotency and atherosclerotic coronary vascular disease.

It is also an object of the invention to provide such device and method that can be cost-effectively manufactured and practiced, respectively.

In brief summary, one aspect of the invention includes a prophylactic system with a vasodilator-containing film for use on a patient's, or user's, body. The prophylactic system includes a first expanse of expandable support material constructed for attachment to a desired section of such a patient's body. A vasodilator-containing film is formed over substantially the entire inner surface of the support material. The first expanse of may be formed as one of the group consisting of a patch, strip, tape, sheath, or condom. In a first preferred embodiment, the first expanse is formed as a sheath and is constructed for enclosing a protuberant section of the patient's body such as an appendage, penis, finger, toe, or ear.

These and other objects and advantages of the invention will be more clearly understood from a consideration of the following description of the preferred embodiments.

DETAILED DESCRIPTION OF THE PREFERRED EMBODIMENT AND

THE PREFERRED MANNER OF PRACTICING THE INVENTION

Figure 1:
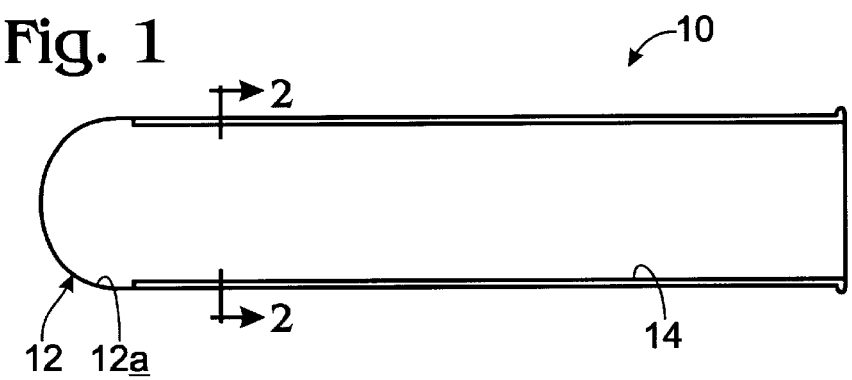
FIG. 1 is a side view of the preferred embodiment of the prophylactic system of the invention.

The preferred embodiment of the prophylactic system of the invention is shown in FIG. 1 at 10 and includes a first expanse 12 of expandable support material constructed for attachment to a desired section of a patient's body, with the support material including an inner surface 12a. An example of support material is a conventional condom. System 10 also includes a vasodilator-containing film 14 formed over substantially the entire inner surface of the support material.

Figure 2:
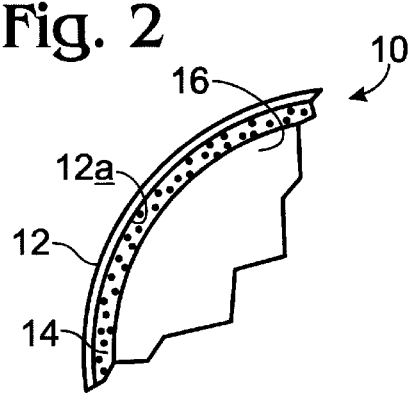
FIG. 2 is a fragmentary cross-sectional view through line 2—2 of FIG. 1.

The rheology of the vasodilator film is to have an optimal viscosity and thixotropy to allow the film to remain on interior surface 12a even when the condom is rolled in the usual way for anti-contamination or sterile packaging. The film must not however be so viscous as to prevent effective transmission of the vasodilator material to the penis, thereby to induce blood flow to the veins of the penis. The film may also be thought of as a coating or as material. The vasodilator may be any known substance that tends to dilate veins/arteries. FIG. 2 shows a fragmentary cross section of system 10 when it is placed over a desired section of a patient's body such as a protuberance like penis 16.

The vasodilator-containing film is formed as a moist composite that includes a vasodilator, such as a nitrate-containing chemical, dispersed in an adhesive carrier. The adhesive carrier is operative to adhere the vasodilator-containing film to the inner surface of the support material, and the vasodilator is in a preselected concentration that effects release into the epidermoid layer of the user's skin when the prophylactic system is placed over the desired section of the user's skin.

Figure 3:
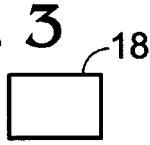
FIG. 3 shows alternate embodiments of a first expanse element of the invention.
Figure 6:
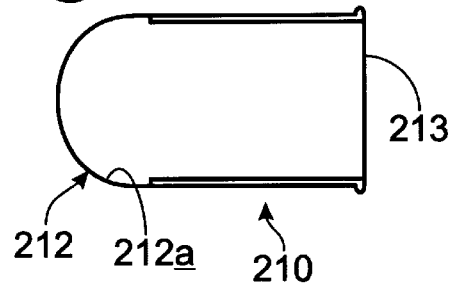
FIG. 6 is a fragmentary view of a fifth embodiment of the invention.

A second preferred embodiment of the prophylactic system further includes a second expanse of expandable support material, with the first expanse being formed as a patch 18, a strip or tape 20 (see FIG. 3), and the second expanse being formed as a sheath or condom (such as expanse 12 in FIG. 1).

Figure 5:
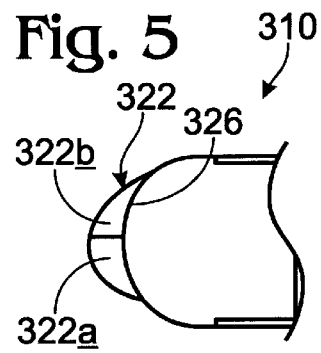
FIG. 5 is a fourth embodiment of the invention.
Figure 4:
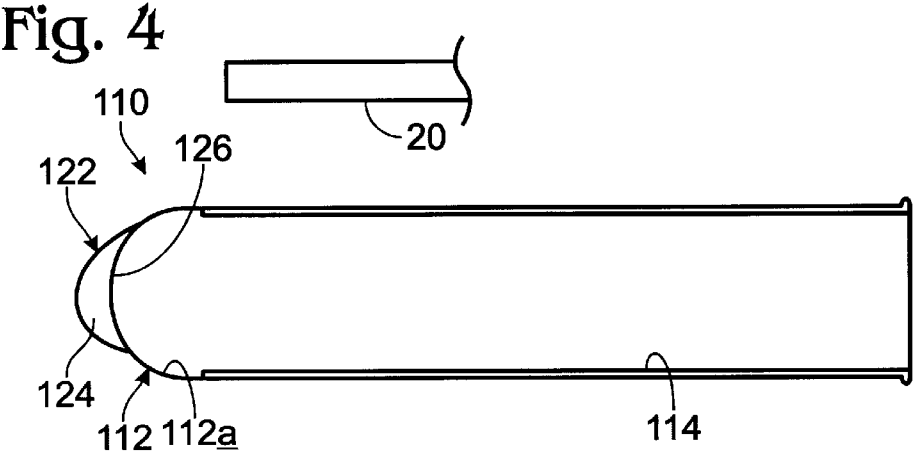
FIG. 4 is a third embodiment of the invention.

Referring to FIG. 4, a third preferred embodiment of the prophylactic system is a condom-like system 110 that includes a sheath 112, and a layer of vasodilator-containing material 114. The sheath is formed as a composite and includes inner layer 114 formed of the vasodilator-containing material. For this embodiment the sheath is preferably constructed for use as a condom to be placed over a penis of a male user, and the sheath includes a first reservoir 122 that holds a preselected amount 124 of the vasodilator-containing material. The sheath also includes a breakable internal membrane 126 defining an inner boundary of the reservoir, with breaking of the internal membrane allowing release of the vasodilator-containing material from the reservoir to allow contact with the penis as a way of promoting a penile erection. The sheath also preferably includes a second reservoir for holding penile ejaculate and that reservoir can take the form of the usual reservoir in conventional condoms. Referring to FIG. 5, the first and second reservoirs may be formed as one reservoir 322 with two compartments 322a, 322b.

A fourth preferred embodiment includes the sheath of the third preferred embodiment and certain other elements including an anti-contamination protector wearable on the hand of the user, and an applicator for applying the vasodilator-containing material to such protuberant section of such user's body.

A fifth preferred embodiment includes the sheath of the third preferred embodiment, and certain other elements including an anti-contamination dispenser for holding a preselected amount of the vasodilator-containing material and for dispensing the vasodilator-containing material on such protuberant section of such users body.

A sixth preferred embodiment (see FIG. 4) includes the sheath of the third preferred embodiment constructed as a penile cap 210 for removably fitting over the head (undepicted) of a penis of a male user. The penile cap includes a penile-head covering 212 and a fastener (such as an elastic band 213) for fastening it to the head of the user's penis.

Another aspect of the invention is a combination method of promoting vasodilation of a penis to facilitate penile erection, and preventing conception. The method includes the steps of applying a vasodilator-containing material topically to such penis to produce a penile erection, and fitting a prophylactic over such penis after such penile erection is produced. For the fitting step, the preferred prophylactic is the prophylactic system described in connection with the system of the invention.

The above devices and methods of the invention meet the above objects by providing devices and methods for the male user to (1) promote desired occurrence of a penile erection, (2) prevent conception and transmission of sexually transmitted diseases such as AIDS, and (3) exhibit other positive health effects such as tending to prevent heart attacks during sexual intercourse in males who have both psychological impotency and atherosclerotic coronary vascular disease.

Accordingly, while a preferred embodiment of the invention has been described herein, it is appreciated that modifications are possible that are within the scope of the invention.

I claim:

1. A condom system for use on a penis of a male user's body, comprising:

a sheath formed as a composite and includes an inner layer formed of a vasodilator-containing material, wherein the sheath is constructed for use as a condom adapted to be placed over a penis of a male user, wherein the sheath includes a first reservoir that holds a preselected amount of the vasodilator-containing material, wherein the sheath includes a breakable internal membrane defining an inner boundary of the reservoir, with breaking of the internal membrane allowing release of the vasodilator-containing material from the first reservoir to allow contact with the penis as a way of promoting a penile erection, and wherein the sheath includes a second reservoir for holding penile ejaculate;

wherein the vasodilator-containing material is formed in a moist composition that includes a vasodilator dispersed in an adhesive carrier, with the adhesive carrier operative to adhere the vasodilator-containing material to the remainder of the sheath and the vasodilator being present in a preselected concentration that is adapted to effect release into an epidermoid layer of the desired section when the system is placed over the desired section.

2. The system of claim 1, wherein the first and second reservoirs are formed as one reservoir with two compartments.

3. A condom system for use on a penis of a male user's body, comprising:

a sheath formed as a composite and includes an inner layer formed of a vasodilator-containing material, wherein the sheath is constructed as a penile cap adapted for removably fitting over the head of a penis of a male user, wherein the cap includes a first reservoir that holds a preselected amount of the vasodilator-containing material, wherein the cap includes a breakable internal membrane defining an inner boundary of the reservoir, with breaking of the internal membrane allowing release of the vasodilator-containing material from the first reservoir to allow contact with the head of the penis as a way of promoting a penile erection, and wherein the cap includes a second reservoir for holding penile ejaculate;

wherein the vasodilator-containing material is formed in a moist composition that includes a vasodilator dispersed in an adhesive carrier, with the adhesive carrier operative to adhere the vasodilator-containing material to the remainder of the cap, and the vasodilator being present in a preselected concentration that is adapted to effect release into an epidermoid layer of the desired section when the system is placed over the desired section.

4. The system of claim 3, wherein the penile cap includes a penile-head covering and a fastener for fastening the penile cap to the head of a penis.

5. The system of claim 4, wherein the penile-head covering is formed as a composite and includes an inner layer formed of the vasodilator-containing material.

6. The system of claim 5, wherein such user has a skin-covered body, and which skin includes an epidermoid layer, and wherein the vasodilator-containing material is formed in a moist composition that includes a vasodilator dispersed in an adhesive carrier, with the adhesive carrier operative to adhere the vasodilator-containing material to the remainder of the penile-head covering, and the vasodilator being present in a preselected concentration that effects release into the epidermoid layer of the desired section when the system is placed over the desired section.

7. The system of claim 6, wherein the penile-head covering includes a first reservoir that holds a preselected amount of the vasodilator-containing material.

8. The system of claim 7, wherein the penile-head covering includes a breakable internal membrane defining an inner boundary of the reservoir, with breaking of the internal membrane allowing release of the vasodilator-containing material from the reservoir to allow contact with the penis as a way of promoting a penile erection.

9. The system of claim 8, wherein the penile-head covering includes a second reservoir for holding penile ejaculate.

10. The system of claim 9, wherein the first and second reservoirs are formed as one reservoir with two compartments.

11. The system of claim 4, further including an anti-contamination protector wearable on the hand of the user, and an applicator for applying the vasodilator-containing material to the penis of the user.

12. The system of claim 4, further including an anti-contamination dispenser for holding a preselected amount of the vasodilator-containing material and for dispensing the vasodilator-containing material on the penis of the user.

13. A condom for use on a penis of a male user, comprising:

a vasodilator cream;

a composite sheath including an inner layer formed of the vasodilator cream;

wherein the sheath includes a first reservoir that holds a preselected amount of the vasodilator cream, and a breakable membrane defining an inner boundary of the reservoir, with breaking of the internal membrane allowing release of the vasodilator cream from the reservoir and to allow contact with the penis as a way of promoting a penile erection, and wherein the sheath includes a second reservoir for holding penile ejaculate;

wherein the vasodilator cream is formed in a moist composition that includes a vasodilator dispersed in an adhesive carrier, with the adhesive carrier operative to adhere the vasodilator cream to the remainder of the sheath and the vasodilator being present in a preselected concentration that is adapted to effect release into an epidermoid layer of the desired section when the condom is placed over the desired section.

14. The system of claim 13, wherein the first and second reservoirs are formed as one reservoir with two compartments.

* * * * *